(12) United States Patent
Waddell (10) Patent No.: US 9,441,845 B2
(45) Date of Patent: *Sep. 13, 2016

(54) ION GENERATION DEVICE

(71) Applicant: Charles Houston Waddell, Roanoke, VA (US)

(72) Inventor: Charles Houston Waddell, Roanoke, VA (US)

(73) Assignee: Global Plasma Solutions, LLC, Savannah, GA (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/918,282

(22) Filed: Jun. 14, 2013

(65) Prior Publication Data

US 2013/0336838 A1    Dec. 19, 2013

Related U.S. Application Data (60) Provisional application No. 61/660,301, filed on Jun. 15, 2012.

(51) Int. Cl.
| | |
|---|---|
| A61L 2/14 | (2006.01) |
| F24F 3/16 | (2006.01) |
| H01J 27/02 | (2006.01) |
| B03C 3/41 | (2006.01) |
| H01T 23/00 | (2006.01) |
| H01T 19/04 | (2006.01) |
| B03C 3/02 | (2006.01) |
| H01J 37/08 | (2006.01) |
| H01J 37/16 | (2006.01) |
| B01D 53/32 | (2006.01) |

(52) U.S. Cl.
CPC .................. *F24F 3/166* (2013.01); *A61L 2/14* (2013.01); *B03C 3/02* (2013.01); *B03C 3/41* (2013.01); *H01J 27/02* (2013.01); *H01J 37/08* (2013.01); *H01J 37/16* (2013.01); *H01T 19/04* (2013.01); *H01T 23/00* (2013.01); *B01D 53/323* (2013.01); *B01D 2257/90* (2013.01); *B01D 2259/4508* (2013.01); *B01D 2259/818* (2013.01); *B03C 2201/10* (2013.01); *F24F 2003/1682* (2013.01); *Y10T 29/49117* (2015.01); *Y10T 29/49169* (2015.01)

(58) Field of Classification Search
CPC ........... A61L 9/015; A61L 9/16; A61L 9/22; A61L 2/14; F24F 3/166; H01T 19/04; H01T 23/00; H01J 37/16; H01J 37/08; H01J 27/02; B03C 3/02; B03C 3/41

See application file for complete search history.

(56) References Cited

U.S. PATENT DOCUMENTS

| | | | | |
|---|---|---|---|---|
| 4,643,745 A | * | 2/1987 | Sakakibara et al. | ............. 96/76 |
| 5,484,472 A | * | 1/1996 | Weinberg | ........................... 96/26 |
| 5,656,063 A | * | 8/1997 | Hsu | ..................... 95/58 |
| 5,667,564 A | * | 9/1997 | Weinberg | ........................... 96/58 |
| 5,702,507 A | * | 12/1997 | Wang | ................................ 96/55 |
| 5,779,769 A | * | 7/1998 | Jiang | ................................. 96/55 |
| 5,814,135 A | * | 9/1998 | Weinberg | ........................... 96/58 |
| 5,911,957 A | * | 6/1999 | Khatchatrian et al. | .. 422/186.07 |

(Continued)

*Primary Examiner* — Regina M Yoo
(74) *Attorney, Agent, or Firm* — Clements Bernard, LLC; Seth L. Hudson (57) ABSTRACT

The present invention provides methods and systems for an ion generation device that includes an elongate housing having a back portion and a pair of side portions extending from the back portion and forming a cavity therein. A conductive portion is disposed within the cavity and connected to a power supply for providing power to the conductive portion. A plurality of tines are engaged to the conductive portion.

14 Claims, 7 Drawing Sheets

(56) References Cited

U.S. PATENT DOCUMENTS

| | | | |
|---|---|---|---|
| 5,975,090 A * | 11/1999 | Taylor et al. | 132/116 |
| 6,118,645 A * | 9/2000 | Partridge | 361/231 |
| 6,182,671 B1 * | 2/2001 | Taylor et al. | 132/116 |
| 6,312,507 B1 * | 11/2001 | Taylor et al. | 96/19 |
| 6,451,266 B1 * | 9/2002 | Lau et al. | 422/186.07 |
| 6,471,753 B1 * | 10/2002 | Ahn et al. | 96/27 |
| 6,504,308 B1 * | 1/2003 | Krichtafovitch et al. | 315/111.91 |
| 6,544,485 B1 * | 4/2003 | Taylor | 422/186.04 |
| 6,585,935 B1 * | 7/2003 | Taylor et al. | 422/29 |
| 6,588,434 B2 * | 7/2003 | Taylor et al. | 132/116 |
| 6,994,733 B2 * | 2/2006 | Bartolone et al. | 8/401 |
| 7,269,873 B2 * | 9/2007 | Brewer et al. | 15/22.1 |
| 7,806,952 B2 * | 10/2010 | Fox et al. | 55/360 |
| 8,861,167 B2 * | 10/2014 | Waddell et al. | 361/231 |
| 9,025,303 B2 * | 5/2015 | Waddell et al. | 361/231 |
| 2001/0048906 A1 * | 12/2001 | Lau et al. | 422/186 |
| 2002/0100488 A1 * | 8/2002 | Taylor et al. | 132/271 |
| 2003/0090021 A1 * | 5/2003 | Kise et al. | 264/113 |
| 2003/0196887 A1 * | 10/2003 | Lau et al. | 204/164 |
| 2004/0065202 A1 * | 4/2004 | Gatchell et al. | 96/66 |
| 2005/0095182 A1 * | 5/2005 | Lee | 422/186.04 |
| 2005/0102768 A1 * | 5/2005 | Bartolone et al. | 8/401 |
| 2007/0248848 A1 * | 10/2007 | Marsh | 429/13 |

* cited by examiner

ION GENERATION DEVICE

CROSS REFERENCE TO RELATED PATENT APPLICATION

The current application claims the benefit of the earlier priority filing of provisional application Ser. No. 61/660,301 that was filed on Jun. 15, 2012.

FIELD OF THE INVENTION

The present invention relates generally to an ion generation device and more generally relates to a ion generation device that includes tines composed of polypropylene impregnated with carbon for discharging ions within the proximate area of the device.

BACKGROUND OF THE INVENTION

Current ionization tubes utilize a cathode that is completely surrounded by a glass tube. The inside of the glass tube contains a wire mesh that serves as an anode. Glass by its very nature has a fragile structure and is prone to breaking. The glass tube in an ionization tube also produces a corona discharge, which minimizes the effect of the ionization tube and increases the amount of energy consumed during operation of ionization tube. The glass tube breaks down over time and must be replaced by the user and the replacement cost for such a tube is high. Additionally, the glass tube requires a voltage high enough to break down the dielectric strength of the glass, and during the break down process, a corona discharge is created, thus causing uncontrolled and undesirable ozone.

For example, U.S. Patent Application No. 2010/0247389 discloses a bipolar ionization tube that has a cathode that is completely surrounded by a glass tube. An anode is provided that circumscribes the interior wall of the glass tube.

There is a need for a bipolar ionization device that is not breakable, eliminates the need for expensive replacement parts, saves energy, provides higher output, and minimizes corona discharge.

BRIEF SUMMARY OF THE INVENTION

According to an embodiment of the present invention, the ion generation device includes an elongate housing having a back portion and a pair of side portions extending from the back portion and forming a cavity therein. A conductive portion is disposed within the cavity and connected to a power supply for providing power to the conductive portion. A plurality of tines are engaged to the conductive portion.

According to another embodiment of the present invention, the ion generation device includes an extrusion disposed within the cavity of the housing.

According to yet another embodiment of the present invention, the ion generation device includes a plurality of tines composed of polypropylene impregnated with carbon.

According to yet another embodiment of the present invention, the ion generation device includes tines that are composed of a homopolypropylene impregnated with carbon.

According to yet another embodiment of the present invention, the ion generation device includes an extrusion composed of rubber having a hollow interior portion for receiving the power supply and conductive portion.

According to yet another embodiment of the present invention, the ion generation device includes a shelf positioned on the inner portion of each side portion of the housing for receiving a first rib of the extrusion.

According to yet another embodiment of the present invention, the ion generation device includes tines that are spaced an equal distance apart along the length of the conductive portion.

According to yet another embodiment of the present invention, the ion generation device includes an elongate housing having a back portion and a pair of side portions having an interior portion and exterior portion and extending generally perpendicularly from the back portion and forming a cavity therein. The extrusion is disposed within the cavity of the housing and having a hollow for receiving a power supply and a conductive portion, wherein the conductive portion includes an elongate portion and a plurality of tines that extend generally perpendicularly outwardly from the elongate portion.

According to yet another embodiment of the present invention, the ion generation device includes an extrusion that has a frustoconical upper portion and a hollow interior portion therein for receiving the power supply and elongate portion of the conductive portion.

According to yet another embodiment of the present invention, the ion generation device includes a plurality of tines extending from the conductive portion and having a lower portion and a top portion, wherein the lower portion is engaged to the conductive portion and is wider than the top portion.

According to yet another embodiment of the present invention, the ion generation device includes an upper end of the tine that contains a point that is from about 0.01 inches to about 0.05 inches in length.

According to yet another embodiment of the present invention, the ion generation device includes an outer housing composed of aluminum.

According to yet another embodiment of the present invention, a method of ionizing air that includes providing an ion generator device that comprises an elongate housing having a back portion and a pair of side portions extending from the back portion and forming a cavity therein. A conductive portion is disposed within the cavity and connected to a power supply for providing voltage to the conductive portion, and a plurality of tines engaged to the conductive portion. An ion generator is placed in an HVAC system that includes a heat transfer device, wherein the ion generator device is positioned next to the heat transfer device.

According to yet another embodiment of the present invention, a method of ionizing air that includes providing an extrusion disposed within the cavity of the housing.

According to yet another embodiment of the present invention, a method of ionizing air that includes providing a plurality of tines extending perpendicularly from the conductive portion and having a lower portion and a top portion, wherein the lower portion is engaged to the conductive portion and is wider than the top portion.

According to yet another embodiment of the present invention, a method of ionizing air that includes a conductive portion composed of polypropylene impregnated with carbon.

According to yet another embodiment of the present invention, a method of ionizing air that includes an ion generation device that is positioned such that air flows perpendicular to the longitudinal length of the tines.

According to yet another embodiment of the present invention, a method of ionizing air that includes a power supply engaged to an electrical connector for supplying power to the power supply.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

Figure 1:
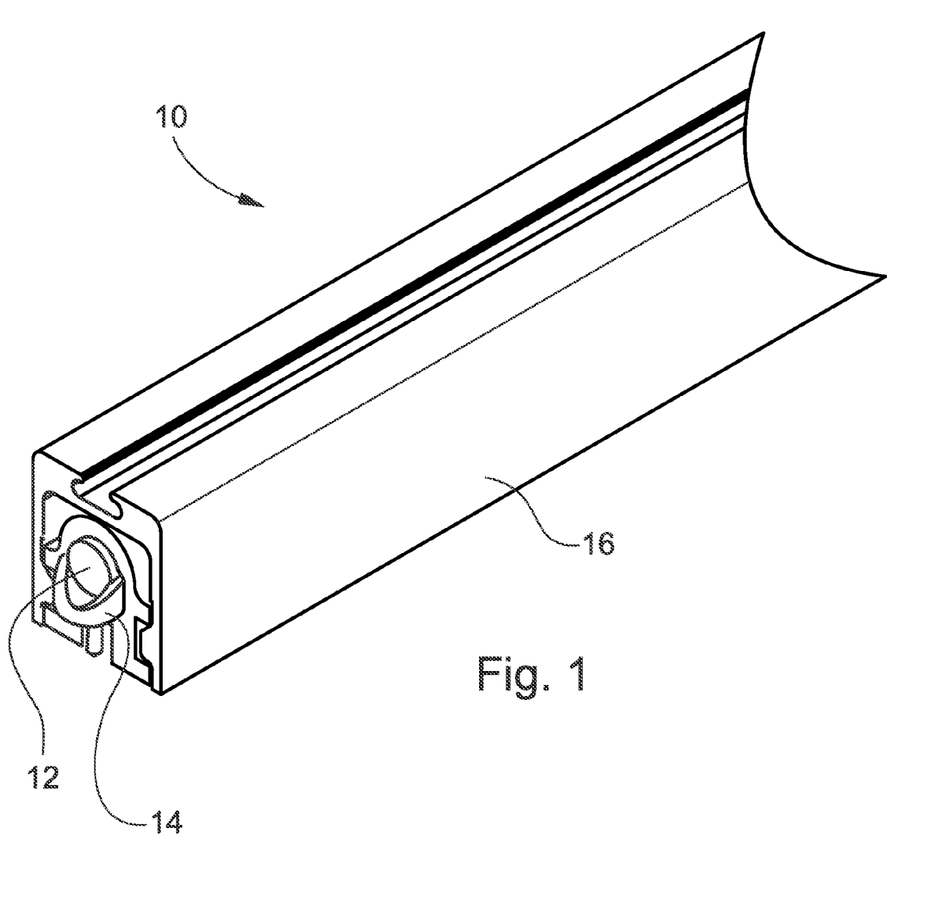
FIG. 1 is a perspective view of the device.
Figure 2:
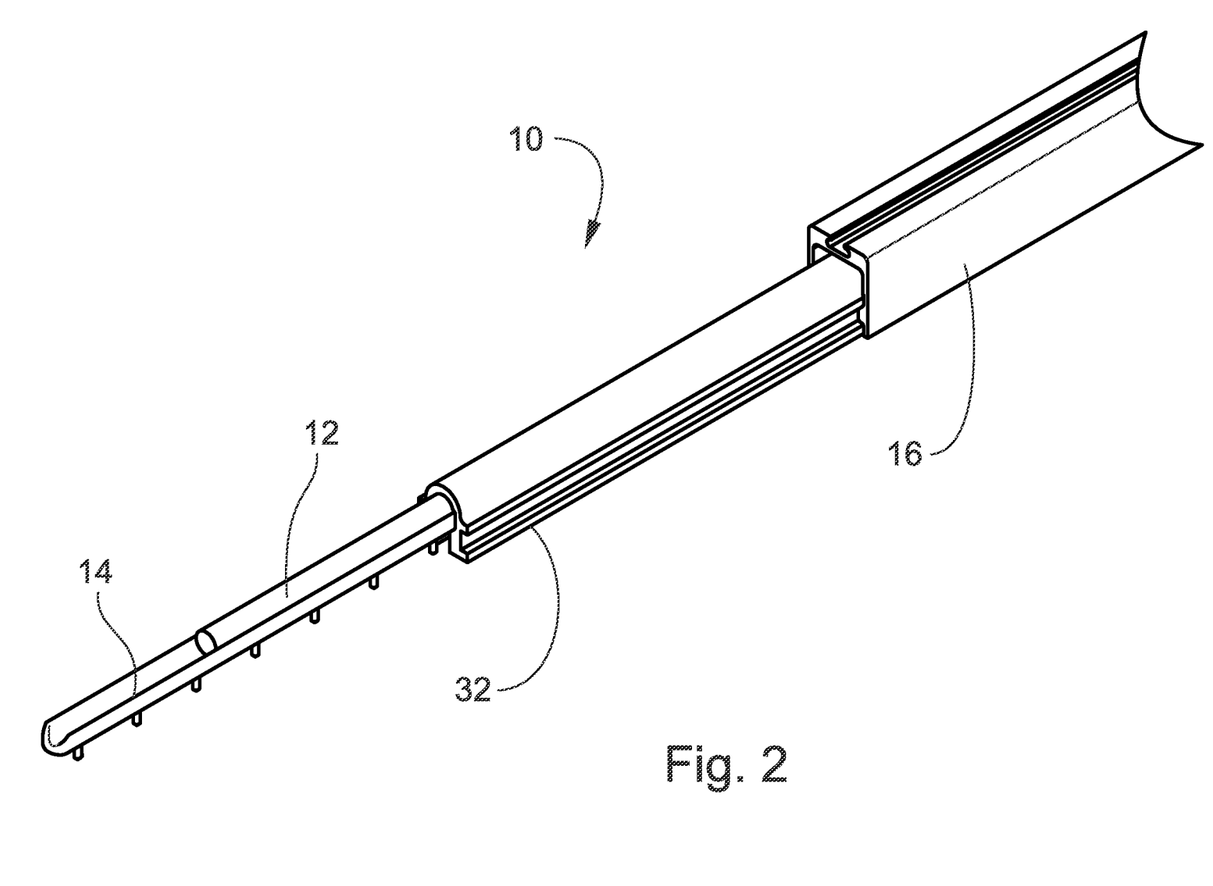
FIG. 2 is a perspective exploded view of the device.
Figure 3:
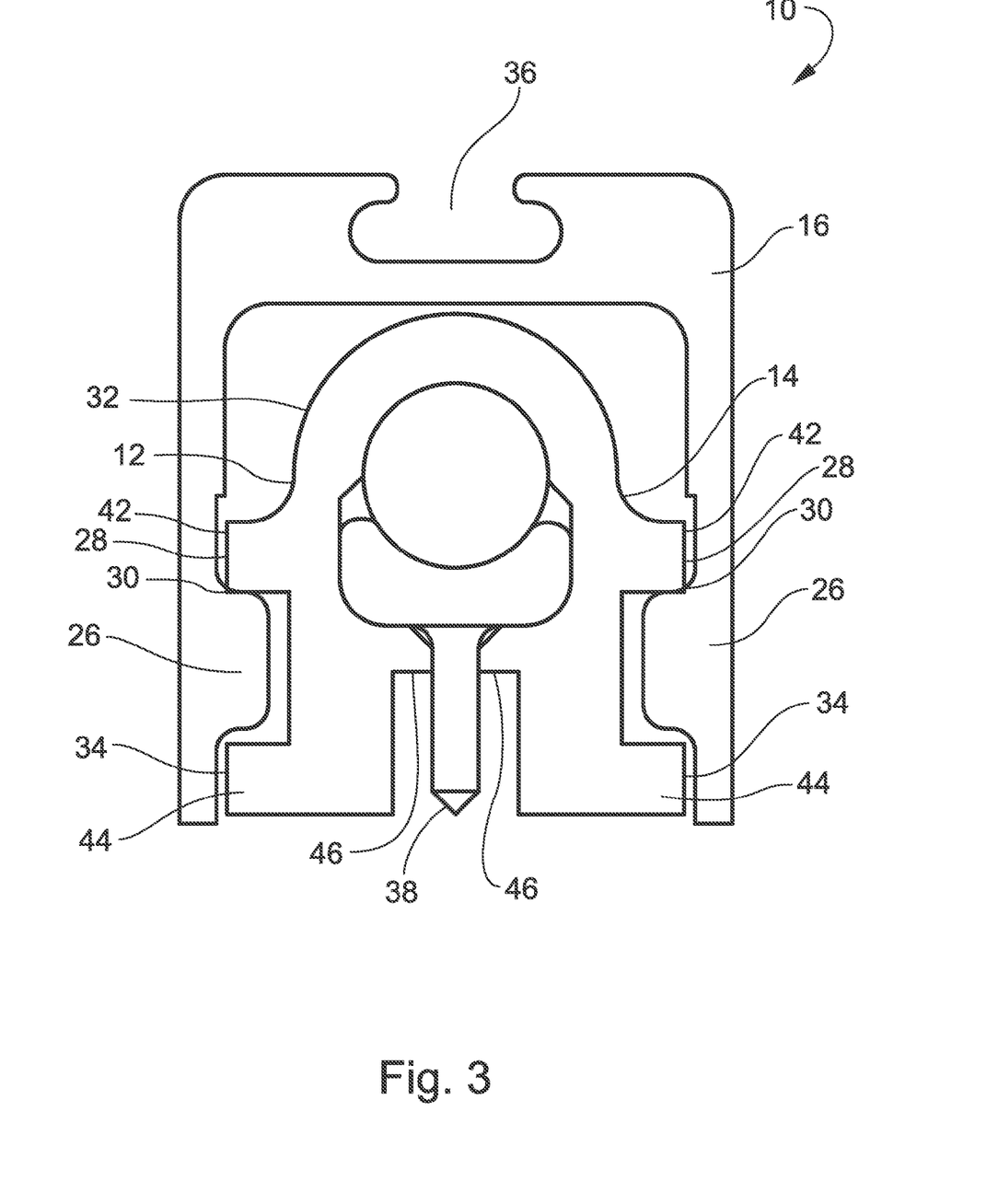
FIG. 3 is a side view of the device.

Referring now specifically to the drawings, an ion generation device is illustrated in FIGS. 1, 2, and 3 and is shown generally at reference numeral 10. The ion generation device 10 generally comprises a power supply 12, a conductive portion 14, and a housing 16. The power supply 12 spans substantially the length of the ion generation device 10 and carries electrical current. The conductive portion 14 also spans substantially the length of the ion generation device 10 and is disposed in close proximity to the power supply 12. The housing 16 contains a cavity 18 for retaining the power supply 12 and a conductive portion 14. Preferably, the housing 16 contains a back portion 20 and two side portions (22, 24) each extending generally perpendicularly from the back portion 20. The cavity 18 is located within the back portion 20 and two side portions (22, 24) and having an opening opposite the back portion 20. The cavity 18 is designed to house, retain, and protect the power supply 12 and conductive portion 14.

Figures 4, 5:
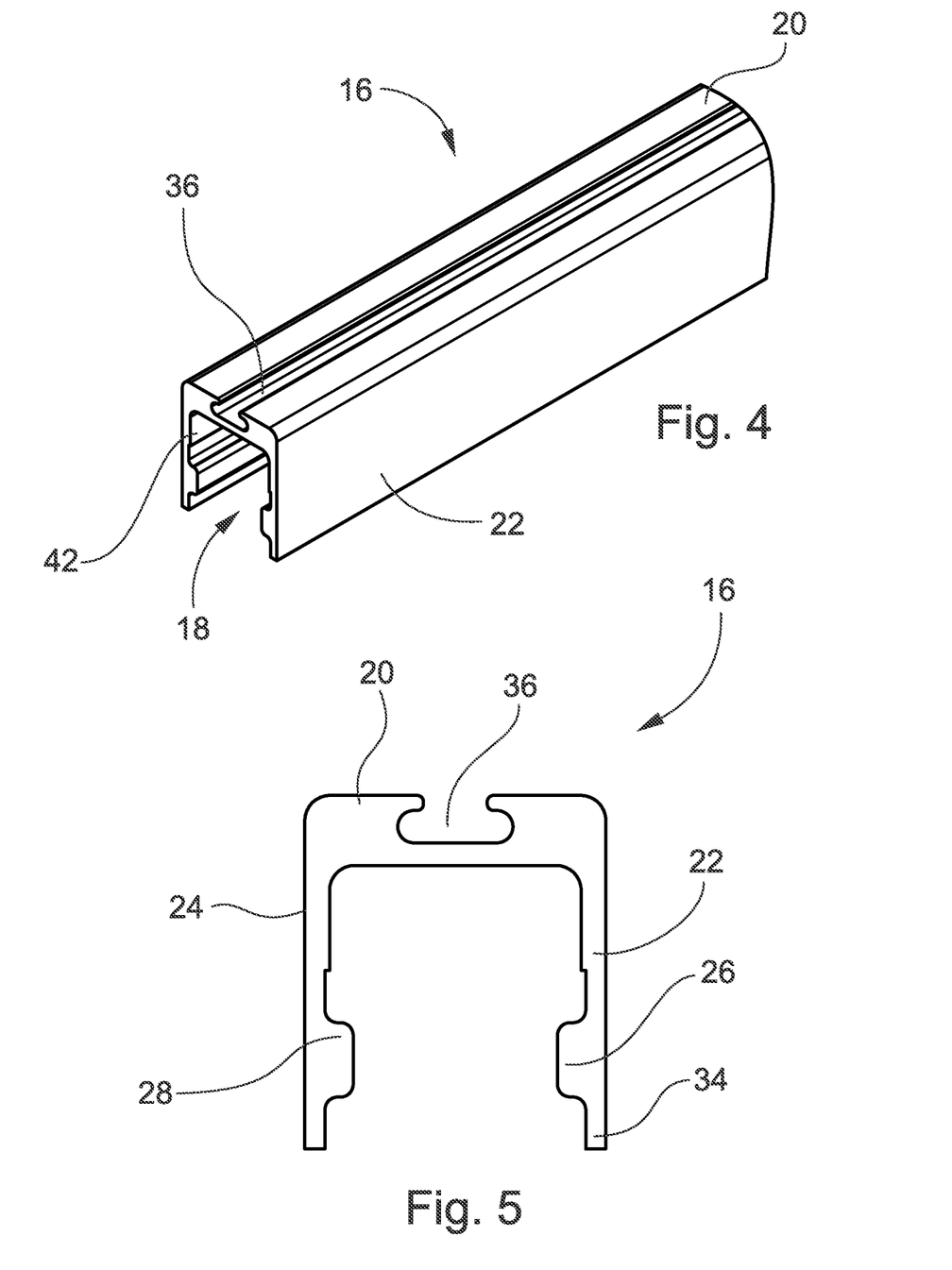
FIG. 4 is a top perspective view of the housing of the device.
FIG. 5 is a side view of the housing of the device.
Figure 6:
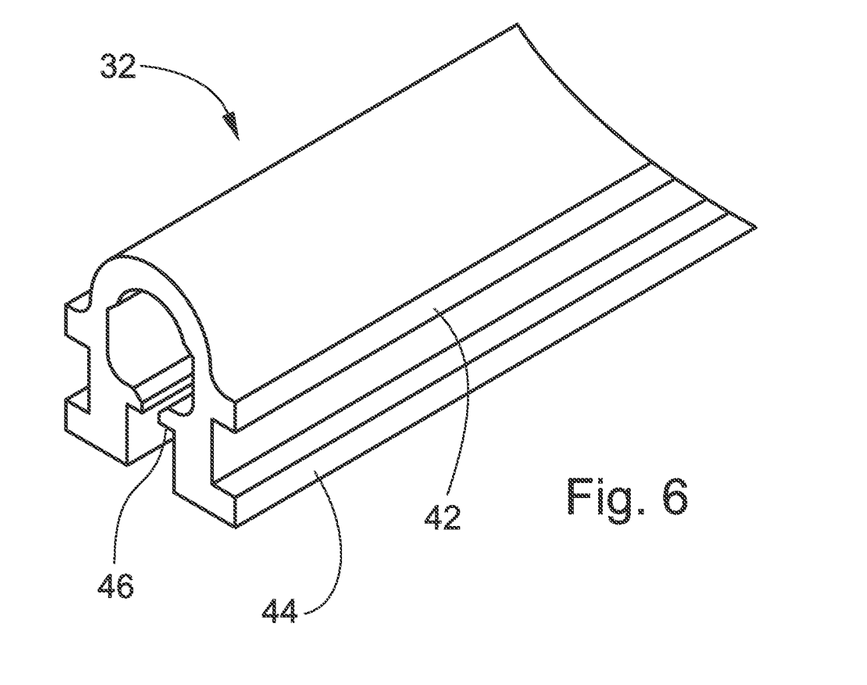
FIG. 6 is a top perspective view of the conductive portion.
Figure 7:
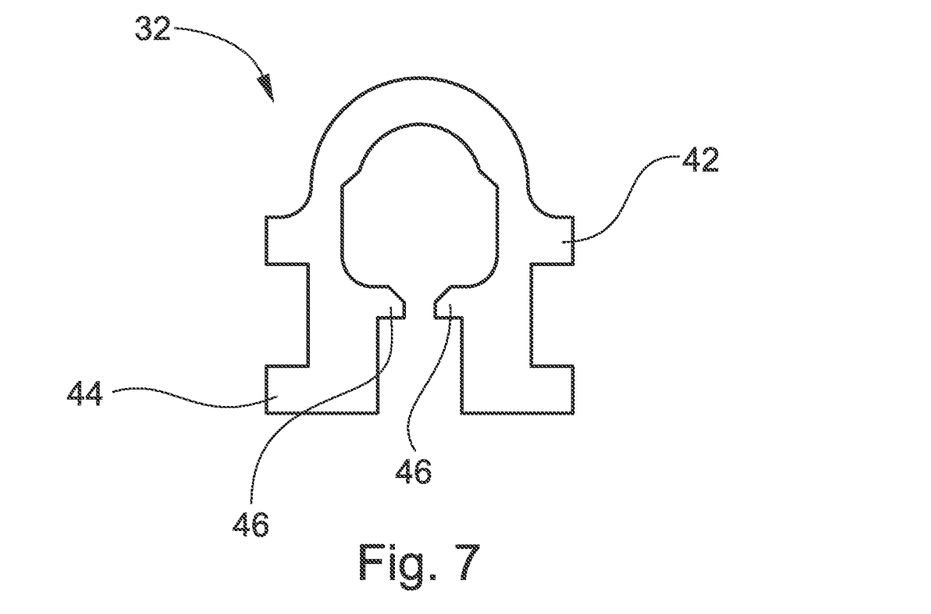
FIG. 7 is a bottom perspective view of the conductive portion.

The cavity of the housing 16 is generally u-shaped. The side portions (22, 24) each have an inner portion and an outer portion, wherein the inner portion is disposed within the cavity 18 and the outer portion forms the exterior of the housing 16. A pair of elongate knobs 26 are formed within the inner portion of each side portion (22, 24) and generally extend along the length of the side portion (22, 24). A first recess 28 is positioned above each knob 26 on the inner portion of each side portion (22, 24). The bottom portion of the first recess 28 and upper portion of the knob 26 form a shelf 30 for positioning an extrusion 32 within the cavity 18 of the housing 16. A second recess 34 is formed within the housing below the knob 26, and preferably the second recess 34 is formed at the upper end of each side portion (22, 24). The second recess 34 is designed to receive a bottom portion of the extrusion 32. The housing 16 may be composed of aluminum or composed of an material with insulative properties such as rubber.

The back portion 20 of the housing 16 has an inner portion and an exterior portion, wherein the inner portion is disposed within the cavity 18 and the outer portion forms the exterior of the housing 16. A channel 36 is disposed on the exterior portion of the back portion 20 of the housing 16 and extends generally along the entire length of the housing 16.

The conductive portion 14 may be made of any material that conducts electricity. In one embodiment, the conductive portion 14 is composed of a thermoplastic polymer imbedded with conductive material that allows the polymer to conduct electricity. For example, the conductive portion 14 may be composed of polypropylene impregnated with carbon. Generally, the conductive portion 14 may contain between about 20 to about 80 wt % polypropylene copolymer, between about 5 to about 40 wt % talc, and from about 5 to 40 wt % carbon black. However, any other resistive, inductive, reactive or conductive plastic or non-metallic material may be utilized for the conductive portion 14.

The ion generator device 10 also includes a plurality of tines 38 disposed on the conductive portion 14. The tines 38 may be embedded into bores in a concave manner or they may extend outwardly in a convex manner. The tines 38 are spaced along the axial length of the top end of the conductive portion 14. The tines 38 contain a base and an upper end. The base of the tines 38 are larger than the upper end. Preferably, the upper end of each tine 38 has a point. In other words, the tines 38 have a base that is integral with the conductive portion 14 and spaced along the axial length of one side of the conductive portion 14 and the top end of the tines 38 forms a point. The conductive portion 14 and tines 38 may be composed of stainless steel, gold, titanium, brass, or any other conductive, but oxidation resistant material, but preferably are formed from a thermoplastic polymer imbedded with conductive material that allows the polymer to conduct electricity. For example, the conductive portion 14 and tines 38 may be composed of polypropylene impregnated with carbon. The tines 38 may contain between about 20 to about 80 wt % polypropylene copolymer, between about 5 to about 40 wt % talc, and from about 5 to 40 wt % carbon black. The conductive portion 14 and tines 38 are preferably formed by injection molding a liquid polypropylene that is impregnated with carbon.

As illustrated in FIGS. 2, 3, 6 and 7, an extrusion 32 may be positioned between the power supply 12 and conductive portion 14 and the housing 16. The extrusion 32 is preferably made of a non-conductive material, such as rubber or plastic, so that the extrusion 32 acts as an insulator between the power supply 12 and conductive portion 14 and housing 16. More preferably, the extrusion 32 is composed of UL V0 rated plastic. The extrusion 32 contains an upper portion and a lower portion. The upper portion of the extrusion 32 is frustoconical and disposed adjacent the inner portion of the back portion of the housing 16. A first pair of ribs 42 extend generally perpendicularly from the extrusion 32 and below the frustoconical upper portion on either side of the extrusion 32. The first pair of ribs 42 are designed to be received within the first recess 28 of the inner portion of each side portion (22, 24) of the housing 16. Each of the first pair of ribs 42 is designed to be engaged to the shelf formed by the bottom portion of the first recess 28 and upper portion of the knob 26. A second pair of ribs 44 are disposed on the lower portion of the extrusion 32 and extend generally perpendicularly from the extrusion 32 and are in a spaced-apart relationship and are generally parallel to the first pair of ribs 42. The second pair of ribs 44 are designed to be disposed within the second pair of recesses 34 of the housing 16.

The tines 38 consist of a base and a stem with a generally consistant and constant diameter that extends to an upper end, containing a point. The point consists of a reduction in the diameter of the stem to a sharp point. The length of the reduction in diameter of the stem to the point is from about 0.01 to about 0.05 inches. In other words, the upper end of the tine 38 contains a point that is from about 0.01 to about 0.05 inches in length.

The frustoconical upper portion of the extrusion 32 contains a hollow for receiving the power supply 12 and conductive portion 14. The hollow is contained within the inner side of the frustoconical upper portion. Two opposed flanges 46 extend angularly downward from the inner side of the extrusion 32 and form the opposed end of the hollow. The tines 38 of the conductive portion 14 extend between the flanges 46 and the flanges 46 provide stability to the tines 38 and to keep the tines 38 properly aligned.

Figure 8:
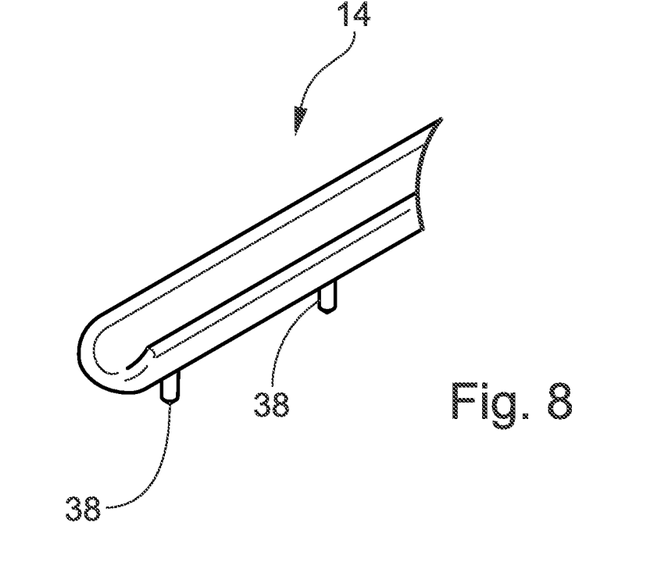
FIG. 8 is a top perspective view of the extrusion.
Figure 9:
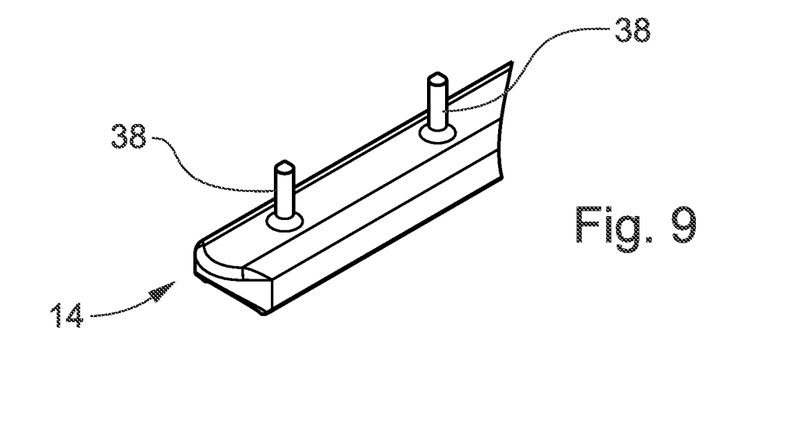
FIG. 9 is a side view of the extrusion.

The conductive portion 14, as shown in FIGS. 8 and 9, contain an elongate rod, whereby the tines 38 extend generally outwardly from the elongate rod. The elongate rod contains a first side and a second side. The first side may be arcuate shaped and designed to receive the generally circular power supply 12. The base of the tines 38 are disposed on the second side of the elongate rod of the conductive portion 14.

The power supply 12 is preferably a generally circular high voltage power supply wire that spans substantially the length of the ion generator device 10. The high voltage wire preferably carries voltage ranging between about 2,000 Volts to about 15,000 Volts, including all points in-between or any voltage and frequency outside these parameters that will cause a cold plasma discharge. The high voltage wire creates a magnetic field and the conductive portion 14, which acts as a resistor, draws the electrons from the magnetic field. The electrons migrate through the conductive portion and progress to the tines 18. The power supply 12 may have an alternating current or direct current component, including a high frequency component that is easy to adjust the ion concentration (e.g. a pulse wave).

The conductive portion 14 and the tines 18 are designed to create positive ions, negative ions, or both simultaneously. The conductive portion 14 and tines 18 are designed to create a differential voltage for attraction or opposition of a flowing median of products within the flowing median, such as contaminants in air and water.

In an exemplary embodiment, when the ions reach the base of the tine 18, the ions flow from the pointed upper end of the tine 18 positioned on the conductive portion 14. The ions flow into the surrounding area and collide with air molecules and particles in the air stream, thus ionizing the air molecules and particles. The ionization of the air aids in cleaning the air, removing odors, and helps reduce pollutants.

In one use, the ion generator device 10 may be installed in a heating, ventilation and air condition (HVAC) system. The ion generator device 10 may be engaged to a structure so that the air flows perpendicular to longitudinal length of the tines 18. In other words, the ion generator device 10 should be positioned such that the tines 18 are upright in relation to the air flow and the air flow is able to flow between the tines 18. In another embodiment, the ion generator device 10 may be installed near a copy machine, industrial machinery, conveyor belts, or generally anywhere where there is a desire to control static electricity.

Figure 10:
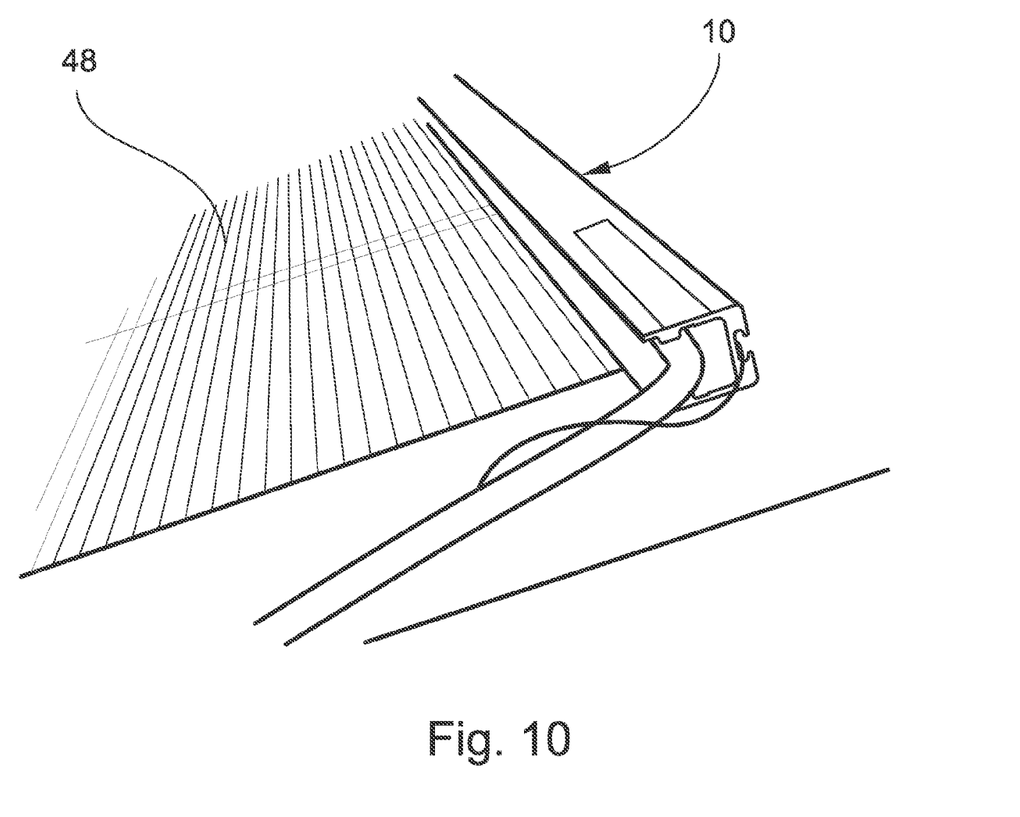
FIG. 10 is a view of the method of using the device.

A horizontal flow, flat heat transfer device 48 is shown in FIG. 10. The device 10 is positioned preferably adjacent the heat transfer device 48 with reference to the air flow. However, it should be understood that the device 10 may be positioned upstream from the heat transfer device 48 if desired by the user. The heat transfer device 48, which is well known in the art, comprises circuited tubes through which refrigerant circulates and may contain a number of substantially flat, planar parallel fins that are attached or adjacent at generally regular spaces on the tubes. The fins increase the effective surface area of the tubes, thereby increasing heat transfer from the air to the surface of the heat transfer device 48. Because of the excellent heat transfer properties, low expense and ease of manufacture of aluminum, a typical heat transfer device 48 may be constructed of aluminum. In determining the spatial relationship between the heat transfer device 48 and the device 10, the objective is to obtain a uniform distribution of the ions across the face of the heat transfer device 48 positioned upstream relative to the air flow.

During use, the power supply 12 is engaged to an electrical connector to supply power to the power supply 12 that in turn supplies power to the power supply 12. The power supply 12 creates a magnetic field and the ions are drawn to the conductive portion 14. The ions progress through the conductive portion 14 and are injected into the tines 18. The ions flow up the tines 18 from the base to the pointed upper end. When the ions reach the pointed upper end of the tine 18, the ions flow from the pointed upper end of the tine 18 and into the surrounding area and collide with air molecules and particles in the air stream, thus ionizing the air molecules and particles. The ionization of the air or other median aids in cleaning the median, removing odors, and helps reduce m contaminants.

In another embodiment, the tines 18 may generate positive and negative ions by utilizing an alternating current or direct-current high voltage power supply with each polarity.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An ion generation device, comprising:
    an elongate housing having a back portion and a pair of side portions extending from the back portion and forming a cavity therein;
    a conductive portion disposed within the cavity and connected to a power supply disposed within the cavity for providing voltage to the conductive portion;
    an insulator disposed between the elongate housing and conductive portion containing a hollow interior portion for receiving the conductive portion and power supply; and
    a plurality of tines engaged to the conductive portion.

2. The ion generation device of claim 1, further comprising an extrusion disposed within the cavity of the elongate housing.

3. The ion generation device of claim 1, wherein the plurality of tines are composed of a polypropylene impregnated with carbon.

4. The ion generation device of claim 1, wherein the plurality of tines are composed of a homopolypropylene impregnated with carbon.

5. The ion generation device of claim 1, further comprising an extrusion composed of UL V0 rated plastic having a hollow interior portion for receiving the power supply and conductive portion.

6. The ion generation device of claim 1, further comprising a shelf positioned on an inner portion of each side portion of the elongate housing.

7. The ion generation device of claim 1, wherein the plurality of tines are spaced an equal distance apart along the length of the conductive portion.

8. An ion generation device, comprising:
   an elongate housing having a back portion and a pair of side portions having an interior portion and exterior portion and extending generally perpendicularly from the back portion and forming a cavity therein;
   an extrusion disposed within the cavity of the elongate housing and having a hollow interior portion for receiving a power supply and a conductive portion, the conductive portion includes an elongate portion and a plurality of tines that extend generally perpendicularly outwardly from the elongate portion and the power supply is disposed between the extrusion and conductive portion.

9. The ion generation device of claim 8, wherein the extrusion contains a frustoconical upper portion and a hollow portion therein for receiving the power supply and elongate portion of the conductive portion.

10. The ion generation device of claim 8, wherein the plurality of tines extending from the conductive portion and having a lower portion and a top portion, wherein the lower portion is engaged to the conductive portion and is wider than the top portion.

11. The ion generation device of claim 8, wherein a top portion of the plurality of tines contains a point that is from about 0.01 inches to about 0.05 inches in length.

12. The ion generation device of claim 8, wherein the conductive portion is composed of polypropylene and impregnated with carbon.

13. The ion generation device of claim 8, wherein the plurality of times are composed of a polypropylene and impregnated with carbon.

14. The ion generation device of claim 8, further comprising an outer housing is composed of aluminum.

* * * * *